(12) United States Patent
Van Holten et al.

(10) Patent No.: US 9,132,040 B2
(45) Date of Patent: Sep. 15, 2015

(54) DRESSING DEVICE

(75) Inventors: Robert W. Van Holten, Flemington, NJ (US); Xintian Ming, Bridgewater, NJ (US); Jerome Riebman, Basking Ridge, NJ (US)

(73) Assignee: Ethicon, Inc., Somerville, NJ (US)

( * ) Notice: Subject to any disclaimer, the term of this patent is extended or adjusted under 35 U.S.C. 154(b) by 972 days.

(21) Appl. No.: 13/298,495

(22) Filed: Nov. 17, 2011

(65) Prior Publication Data

US 2013/0131621 A1 May 23, 2013

(51) Int. Cl.
| | |
|---|---|
| A61L 15/16 | (2006.01) |
| A61K 9/70 | (2006.01) |
| A61F 13/00 | (2006.01) |
| A61K 31/155 | (2006.01) |
| A01N 25/04 | (2006.01) |
| A01N 25/34 | (2006.01) |
| A01N 31/02 | (2006.01) |

(52) U.S. Cl.
CPC .......... *A61F 13/00063* (2013.01); *A01N 25/04* (2013.01); *A01N 25/34* (2013.01); *A01N 31/02* (2013.01); *A61F 13/00021* (2013.01); *A61K 31/155* (2013.01); *A61F 2013/00182* (2013.01)

(58) Field of Classification Search
CPC ......... A61F 13/02; A61F 13/06; A61F 13/15; A61K 9/70; A61L 15/16; A61L 15/20; A61L 15/22; A61L 15/24; A61L 15/42; A61L 15/58; A61L 15/60; A61L 15/62; A61M 1/00
See application file for complete search history.

(56) References Cited

U.S. PATENT DOCUMENTS

| | | | |
|---|---|---|---|
| 3,918,446 | A | 11/1975 | Buttaravoli |
| 4,324,237 | A | 4/1982 | Buttaravoli |
| 4,915,694 | A | 4/1990 | Yamamoto |
| 5,372,589 | A | 12/1994 | Davis |
| 5,554,106 | A | 9/1996 | Layman Spillar |
| 5,571,079 | A | 11/1996 | Bello |
| 5,620,419 | A | 4/1997 | Lui |
| 5,686,096 | A | 11/1997 | Khan |
| 5,833,665 | A | 11/1998 | Bootman |
| 5,968,000 | A | 10/1999 | Harrison |
| 6,124,521 | A | 9/2000 | Roberts |
| 6,368,611 | B1 | 4/2002 | Whitbourne |
| 6,765,122 | B1 | 7/2004 | Stout |
| 6,787,682 | B2 | 9/2004 | Gilman |
| 6,884,920 | B2 | 4/2005 | Worthley |
| 7,137,968 | B1 | 11/2006 | Burrell |
| 7,723,559 | B2 | 5/2010 | Linnane |
| 7,858,838 | B2 | 12/2010 | Holm |
| 2003/0153860 | A1* | 8/2003 | Nielsen et al. .................. 602/43 |
| 2006/0068014 | A1 | 3/2006 | Munro |
| 2007/0282237 | A1 | 12/2007 | Munro |
| 2011/0190722 | A1 | 8/2011 | Munro |

* cited by examiner

*Primary Examiner* — Melanie Hand

(57) ABSTRACT

The invention relates to a transparent, absorbent device for the dressing of wounds and insertion sites of percutaneous and drug delivery devices. The device provides 360 degree or complete circumferential protection of a wound or insertion site of a percutaneous or drug delivery device and comprises a hydrogel center and at least one absorbent material. The hydrogel center can optionally comprise a bioactive agent(s).

17 Claims, 9 Drawing Sheets

FIGURE 2
2a
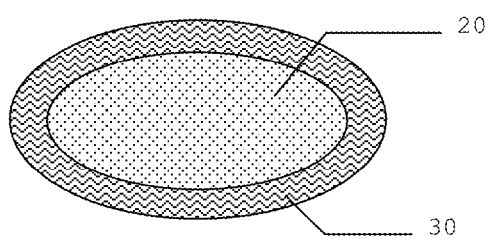
2b
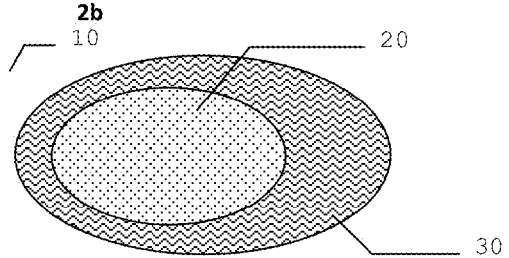
2c
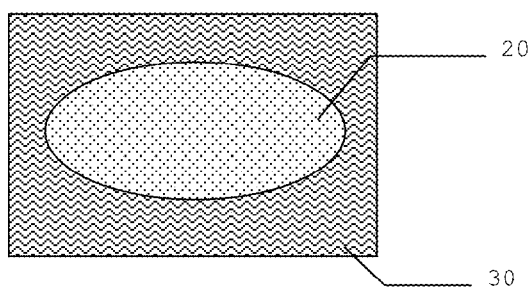
2d
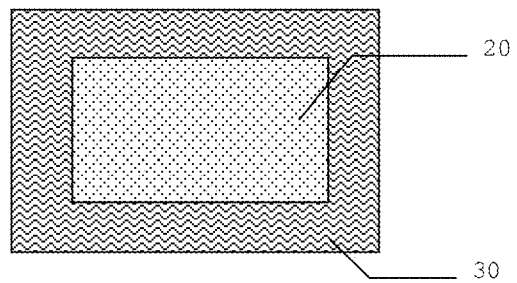
2e
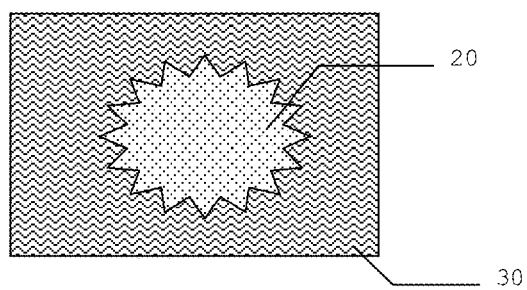
2f
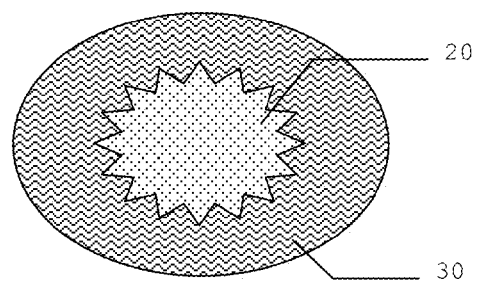

FIGURE 3
3a
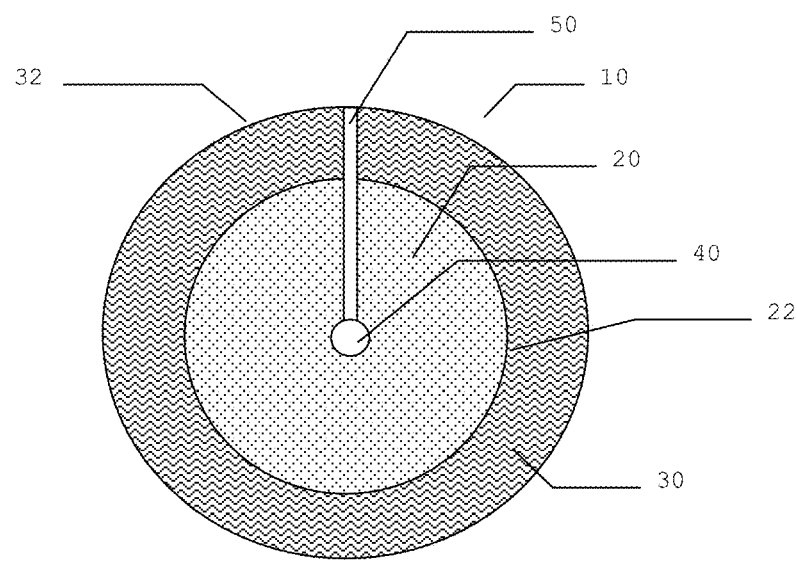
3b
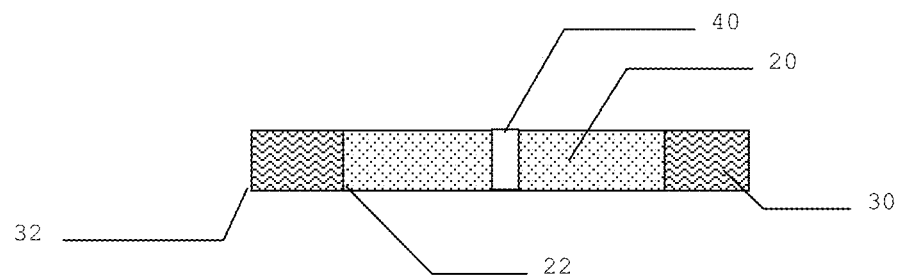
3c
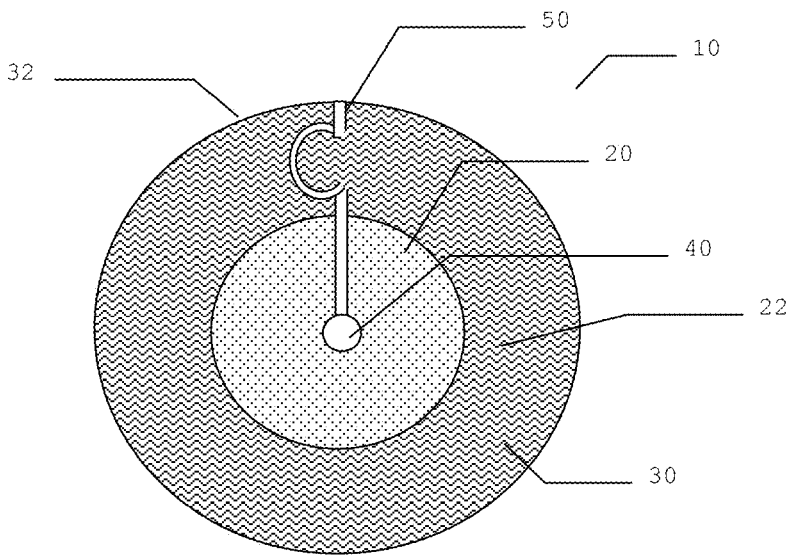

DRESSING DEVICE

FIELD OF THE INVENTION

The invention relates to a transparent, absorbent device for the dressing of wounds and insertion sites of percutaneous and drug delivery devices. In particular, the device provides 360 degree or complete circumferential protection of a wound or insertion site of a percutaneous or drug delivery device and comprises a hydrogel center and an absorbent material surrounding the hydrogel center.

BACKGROUND OF THE INVENTION

Hospitals employ multiple strategies to prevent and/or reduce wound infections and infections associated with the use of percutaneous and drug delivery medical devices, such as antiseptic preparation of wounds and insertion sites. Such strategies include the initial application of topical antimicrobial solutions such as alcohol or iodine. Topical ointments, such as ointments containing neomycin, polymyxin and bactracin, and dressing devices have also been shown to prevent wound infections and catheter colonization/infection.

Many types of dressings are known for the treatment of wounds and insertion sites of percutaneous and drug delivery devices. Cuffs impregnated with an antimicrobial agent have been used to attach to catheters. Johnson & Johnson Corporation markets a commercially available cuff product sold under the trade mark BIOPATCH® that is applied around percutaneous devices to prevent localized infection at the insertion site. This product is a foam material that contains the antimicrobial agent chlorhexidine gluconate (CHG). Efforts to coat the catheters with antimicrobial agents are also known.

Recently transparent film dressings, that allow a visual check on a catheter insertion site, have been used as described in U.S. Pat. No. 5,372,589, issued Dec. 13, 1994 to Davis. Centurion Medical Products markets a commercially available catheter site dressing with antimicrobial properties sold under the trademark SorbaView® SHIELD. The 3M Company also markets a commercially available intravenous (IV) site transparent dressing sold under the trademark Tegaderm™-CHG (clorhexidine gluconate) that is designed to reduce the incidence of catheter-related bloodstream infections (CRBSI), with the CHG being the antimicrobial agent. The CHG is intended to elute from a pad that is transparent and covered with an adhesive bandage layer. The device, however, fails to provide 360 degree or complete circumferential coverage around the insertion site, and the CHG eluting portion of the device is not placed underneath the catheter which may further limit its effectiveness. The device transparency is also compromised when placed in an area with oozing blood and/or exudates.

Securement devices are also known, such as U.S. Pat. No. 3,918,446, issued Nov. 11, 1975 to Buttaravoli, that assist with keeping a percutaneous device in place. The device of U.S. Pat. No. 3,918,446 has an upper and a lower pad, between which the intravenous device is fixed. Since the function of the device is to secure the device to the body, there is a teaching to provide an adhesive material to the bottom of lower pad, and to the bottom of the top pad. U.S. Pat. No. 3,918,446 discusses providing the adhesive with an antibacterial agent, and the device of this patent teaches including a slit in the bottom pad of the dressing, which lies below the intravenous needle or catheter when the device is in place, allowing the intravenous device to remain in contact with the skin, and therefore limiting the infection control of the device.

U.S. Pat. No. 5,833,665 issued to Matthew Bootman et al. is directed to a wound dressing for percutaneous catheters that is comprised of a cross linked polymer containing a bioactive agent. U.S. Pat. No. 5,833,665 discloses a radial slit that is made in the device so that it can be deployed over an already placed catheter. It also discloses and claims the use of adhesives for securing the device.

U.S. Pat. No. 6,368,611 entitled "Anti-infective covering for percutaneous and vascular access device and coating method" and issued to Whitbourne discloses a device comprising a disc provided with an antimicrobial composition, wherein the composition comprises at least one antimicrobial agent exhibiting antimicrobial activity when in a substantially dry state or when solvated after being in a substantially dry state. The disc surrounds and abuts an inserted surface of an insertable medical device when a portion of the inserted surface projects from a bodily surface; the disc is in contact with the bodily surface.

In addition to infection control and transparency, there is a need for absorbent dressings to wick away blood and exudates. U.S. patent application Ser. No. 10/515,028 entitled "Ionic hydrogels with controlled aqueous fluid absorption" and published on Mar. 30, 2006, as U.S. Patent Publication No. 2006/0068014 A1 discloses cross-linked plasticized polymeric hydrogels suitable for use in skin contacting applications that can be used in association with medical, health and personal care products such as passive drug delivery devices and wound dressings.

U.S. patent application Ser. No. 13/054,208 entitled "Compositions for use as or in wound dressings" and published on Aug. 4, 2011, as U.S. Patent Publication No. 2011/0190722 A1 discloses a composition for the treatment of a wound wherein the composition comprises a first layer, which comprises a porous, optionally hydrophilic material capable of absorbing fluid from the wound at least in part by capillary action, and a second layer comprising an absorbent hydrogel. The first layer is associated with the second layer, and, in the treatment, the first layer is disposed closer to the wound than the second layer.

U.S. patent application Ser. No. 11/840,536 entitled "Absorbent materials and articles" and published on Dec. 6, 2007, as U.S. Patent Publication No. 2007/0282237 A1 discloses an absorbent material that comprises a flexible, skin-conformable, moisture-absorbent sheet member, optionally a net member in sheet form overlying and associated with the absorbent sheet member on at least one face thereof, and a hydrogel disposed on at least one of the net member, when present.

A number of other patents teach various types of related dressings, including U.S. Pat. No. 4,324,237 to Buttaravoli; U.S. Pat. No. 5,571,079 to Bello et al.; U.S. Pat. No. 5,686,096 to Khan; U.S. Pat. No. 6,765,122 to Stout; U.S. Pat. No. 7,137.968 to Burell; and U.S. Pat. No. 7,858,838 to Holm et al. A number of other patents teach various single slit embodiments, such as U.S. Pat. Nos. 4,915,694; 5,554,106; 5,620,419; 5,968,000; 6,765,122; and 7,723,559. Other related references include U.S. Pat. No. 6,787,682 entitled "Absorbent foam wound dressing" and issued to Gilman; U.S. Pat. No. 6,124,521 entitled "Dermal wound window dressing securement system" and issued to Roberts; and U.S. Pat. No. 6,884,920 entitled "Hydrocolloid window catheter dressing and a method for making and using the same" and issued to Worthley.

There is a need, however, to provide an improved exudates absorbing device for complete or 360 degree or complete circumferential protection of a wound or percutaneous or drug delivery device insertion site. It is an object of the present invention to provide wound dressing device having transparency for inspecting the conditions of the wound or skin penetration site and absorbency to wick away blood and exudates to prevent maceration of the skin and the reduction in the transparency to the wound site. It is another object of the present invention to provide a dressing device having a transparent hydrogel center and an absorbent material to wick away blood and remove exudates wherein the hydrogel center can optionally comprise a bioactive agent to deliver antimicrobial and/or other wound healing factors at the wound site or site of the insertion of a percutaneous or drug delivery device into the body.

These and other objects of the present invention will be apparent from the following description and appended claims, and from practice of the invention.

SUMMARY OF THE INVENTION

The present invention is directed to a wound dressing for use with a percutaneous or drug delivery device that has punctured the skin of a patient and which has a portion of the percutaneous medical device protruding from the skin. One type of such a percutaneous device is a catheter, such as a temporary installed catheter or longer term in-dwelling catheter. The dressing of the present invention provides an improved exudates absorbing function for 360 degree or complete circumferential protection of a wound or percutaneous or drug delivery device insertion site, with the device having transparency for inspecting the conditions of surgical wound and/or of the skin penetration site and sufficient absorbency to effectively wick away blood and exudates. The device can optionally comprise antimicrobial properties.

In one embodiment, the wound dressing comprises a transparent hydrogel center and an absorbent material surrounding a periphery of the transparent hydrogel center. In some embodiments, the wound dressing is adapted for use with a percutaneous or drug delivery medical device that has punctured the skin of a patient and has a portion of the percutaneous or drug delivery medical device protruding from the skin. In these embodiments, the wound dressing further comprise an aperture in the hydrogel center and a slit connecting a periphery of the absorbent material with the aperture. In other embodiments, the hydrogel center can further comprise a bioactive agent(s). In other embodiments, the wound dressing can further comprise an optional barrier coating or barrier film in order to prevent migration of the bioactive agent into the absorbent material. In yet another embodiment, the hydrogel center further comprises a hemostatic coating. In another embodiment, the hydrogel center comprises a plurality of surface channels to carry exudates by capillary action towards the absorbent material.

In another embodiment, the wound dressing comprises a transparent hydrogel center; a first absorbent material layer comprising an internal portion, a peripheral portion, and a centrally disposed aperture; and a second absorbent material layer comprising an internal portion, a peripheral portion, and a centrally disposed aperture. In this embodiment, the first and second absorbent material layers are joined together at the peripheral portions of the first and second absorbent material layers and a gap is formed between the first and second absorbent material layers at the internal portions of the first and second absorbent material layers. The hydrogel center is disposed in the centrally disposed apertures of the first and second absorbent material layers and a periphery portion of the hydrogel center is within the gap formed between the first and second absorbent material layers. In this double absorbent material layer embodiment, the hydrogel center free floats in the gap between the first and second absorbent material layers, and the wound dressing can be adapted for use with a percutaneous or drug delivery medical device that has punctured the skin of a patient and has a portion of the percutaneous or drug delivery medical device protruding from the skin. In these embodiments, the wound dressing further comprise an aperture in the hydrogel center and a slit connecting a periphery of the absorbent material with the aperture.

In another embodiment of the double absorbent material layer embodiment, the hydrogel center further comprises a bioactive agent(s) and/or a hemostatic coating. In another embodiment, the hydrogel center comprises a plurality of surface channels to carry exudates by capillary action towards the absorbent material. In yet another embodiment of the double absorbent material layer embodiment, the wound dressing comprises a transparent film disposed between the hydrogel center and the absorbent material of the first and second layers to prevent sticking of the hydrogel center to the first and second absorbent material layers.

The material used for the absorbent material and absorbent material layers of the wound dressings discussed herein comprise a woven or non-woven felt or foam selected from the group consisting of polyurethane, polyester, cellulose, alginate, polyacrylates, polyolefins, and cottons. The hydrogel centers of the wound dressings of the invention comprise a hydrogel material selected from the group consisting of polyethylene oxide, polypropylene oxide, poloxamer, 2-acrylamido-2methypropane sulphonic acid, 3-sulphopropylacrylate, polyvinylpyrrolidone, polyethylene glycol, polylactic acid, polyvinylalcohol, polyacrylamides, silicone, agarose, methylcellulose, hyaluronan, collagen-acrylate, and polyethylene glycol co-peptides.

The bioactive agents suitable for use with the wound dressings of the invention comprise one or more antimicrobial agents selected from the group consisting of chlorhexidine gluconate, chlorhexidine acetate, silver iodide, silver bromide, silver chloride, nano-particulate metallic silver, benzalkonium chloride, polyhexamethylene biguanide, Triclosan, metronidazole, alcohol, or iodine.

BRIEF DESCRIPTION OF THE FIGURES

FIG. 1a illustrates a perspective view of an embodiment of a dressing device according to the present invention.

FIG. 1b illustrates a cross section view of the device shown in FIG. 1a.

FIGS. 2a-2f illustrate perspective views of variously shaped embodiments of dressing devices according to the present invention.

FIG. 3a illustrates a perspective view of another embodiment of the inventive dressing device shown in FIG. 1a further comprising an aperture in the center and a slit connecting a periphery of the device with the aperture.

FIG. 3b illustrates a cross section view of another embodiment of the inventive dressing device shown in FIG. 1a further comprising an aperture in the center.

FIG. 3c illustrates a top view of another embodiment of the inventive dressing device shown in FIG. 1a with an optional slit in non-linear or curved configuration.

FIG. 9a illustrates a perspective view of another embodiment of the inventive dressing device according to the present invention.

FIG. 9b illustrates a cross section view of the device shown in FIG. 9a.

DETAILED DESCRIPTION OF THE INVENTION

It is an object of the present invention to provide an improved exudates absorbing device to serve as dressings for wounds and insertion sites of percutaneous and drug delivery devices. The device of the present invention provides 360 degree protection of wounds or insertion sites of percutaneous or drug delivery devices and comprises a hydrogel center and an absorbent material surrounding the hydrogel center for wicking away blood and exudates. The device of the present invention has transparency for inspecting the conditions of the skin penetration site and can optionally have antimicrobial properties.

It is an object of the present invention to provide a wound dressing that is easily applied and is made of a polymer which can serve as a delivery vehicle for controlled release of a bioactive agent entirely around a wound or insertion site of a percutaneous or drug delivery device. These and other objects of the invention will be apparent from the following description and appended claims and from practice of the invention.

Figure 1:
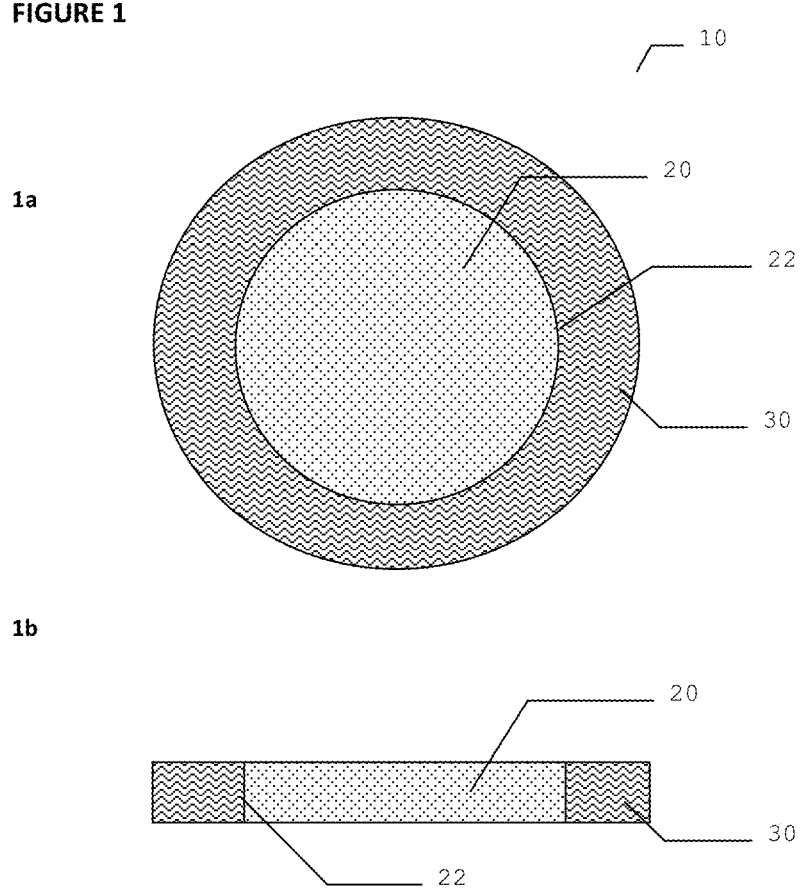

Referring to FIG. 1a, illustrated is a perspective view of an embodiment of a dressing device 10 according to the present invention comprising a transparent or semi-transparent hydrogel center 20 that can optionally be impregnated with a bioactive agent. In one embodiment, the bioactive agent is an antimicrobial agent. The hydrogel center 20 is surrounded in its periphery 22 by an absorbent material 30 made of foam, fabric, non-woven, or fiber structure or other suitable material. In one embodiment, the hydrogel center 20 and absorbent material 30 are disposed side-by-side. In this embodiment, for example, the hydrogel can be attached to the absorbent material by pouring a polyethylene oxide (PEO), hydrogel feed mix gel (AquaMed Technology Inc.) into a foam cavity and cross linking the PEO. The hydrogel center 20 is formed in a shape of a substantially flat disk of circular or elliptical shape. The absorbent material 30, such as polyurethane foam, can be attached to the hydrogel center 20 by having an oversized supportive scrim, typical of that used in the industry, so that the scrim could be spot welded, glued or crimped onto the absorbent material or foam. In FIG. 1b, a cross sectional view of the embodiment shown in FIG. 1a is illustrated.

In one embodiment, the absorbent material 30 is used as a mold during casting of the hydrogel to create an integrated structure. In another embodiment, the absorbent material 30 and the hydrogel center 20 are attached to one another by a supporting structure such as scrim or other film layer coating. In another embodiment, there is a circular void or cut-out in the absorbent material 30 into which the hydrogel center 20 is inserted. In another embodiment, the hydrogel can be cut to a 16 mm diameter disk and placed in a slit within the absorptive material 30, such as polyurethane foam. The slit sides of the absorbent material 30 are designed to hold the hydrogel center 20 in intimate contact with the skin. In one embodiment, the hydrogel is shaped on a contour that places a significant portion of the hydrogel center imbedded within the absorptive material 30.

As illustrated in FIGS. 2a-2f, which show perspective views of variously shaped embodiments of a dressing device according to the present invention, other geometrical shapes of the hydrogel center 20 are contemplated such as circular, elliptical, rectangular, star-shaped, and other shapes. The outer absorbent material 30, formed by die-cutting foam, fabric, non-woven, or fiber structure or other suitable material to a thickness of 1 mm to 4 mm and in a circular or elliptical shape, surrounds the periphery 22 of the hydrogel center 20. In one embodiment, the absorbent material 30 is disposed side-by-side with the hydrogel center 20, and in another embodiment the absorbent material 30 overlaps the hydrogel center 20 by 1 mm to 3 mm. Other geometrical shapes of the outer absorbent material 30 are contemplated such as rectangular, elliptical, star-shaped, and other shapes as illustrated in FIGS. 2a-2f. In all embodiments, the periphery 22 of the hydrogel center 20 is fully surrounded by the outer absorbent material 30.

FIG. 3a illustrates a perspective view of another embodiment of the inventive dressing device 10 shown in FIG. 1a further comprising an aperture 40 in the center and a slit 50 connecting a periphery 32 of the absorbent material 30 or device 10 with the aperture 40. FIG. 3b illustrates a cross section view of another embodiment of the inventive dressing device shown in FIG. 1b further comprising an aperture in the center. The aperture 40 and slit 50 can be formed by cutting, punching, or similar after the dressing device 10 is constructed. FIG. 3c illustrates a top view of another embodiment of the inventive dressing device shown in FIG. 1a with an optional slit in non-linear or curved configuration, which can be zigzag, angled, kidney-shaped.

The embodiments illustrated in FIGS. 3a, 3b, and 3c are adapted for use with a percutaneous or drug delivery medical device (not shown) that has punctured the skin of a patient and has a portion of the percutaneous or drug delivery medical device protruding from the skin. One type of such a percutaneous device is a catheter, such as a temporary installed catheter or longer term in-dwelling catheter. The dressing device 10 of the present invention is adapted for installation over a site of the insertion of the catheter into the body by having an optional aperture 40 for accommodating the catheter and an optional slit 50 for facilitating the installation of the dressing device over the catheter. The dressing device 10 provides an improved exudates absorbing function for 360 degree or complete circumferential protection of the catheter insertion site, with the device having transparency for inspecting the conditions of the skin penetration site and sufficient absorbency to effectively wick away blood and exudates. The dressing device 10 can also provide improved antimicrobial function for 360 degree protection of a wound or catheter insertion site by having antimicrobial properties.

The aperture 40 has a shape and diameter to accommodate the percutaneous or drug delivery medical device protruding from the skin. In one embodiment, the diameter of the circular aperture 40 is equal to the outside diameter of a catheter or is larger than the outside diameter of a catheter by 0.001 mm-1 mm. In some embodiments, the diameter of aperture 40 is from about 0.3 mm to about 15 mm. In another embodiment, the diameter of aperture 40 is from about 1 mm to about 8 mm. The width of slit 50 is adapted to facilitate installation over the already installed indwelling catheter. The width of slit 50 ranges from about 0.01 mm to about 2 mm. In another embodiment, the width of slit 50 ranges from about 0.1 mm to 1.0 mm. The slit 50 of the device can be created after loading of the hydrogel center 20 with a bioactive agent(s) and attaching the absorbent material 30 to the hydrogel center 20.

Figure 4:
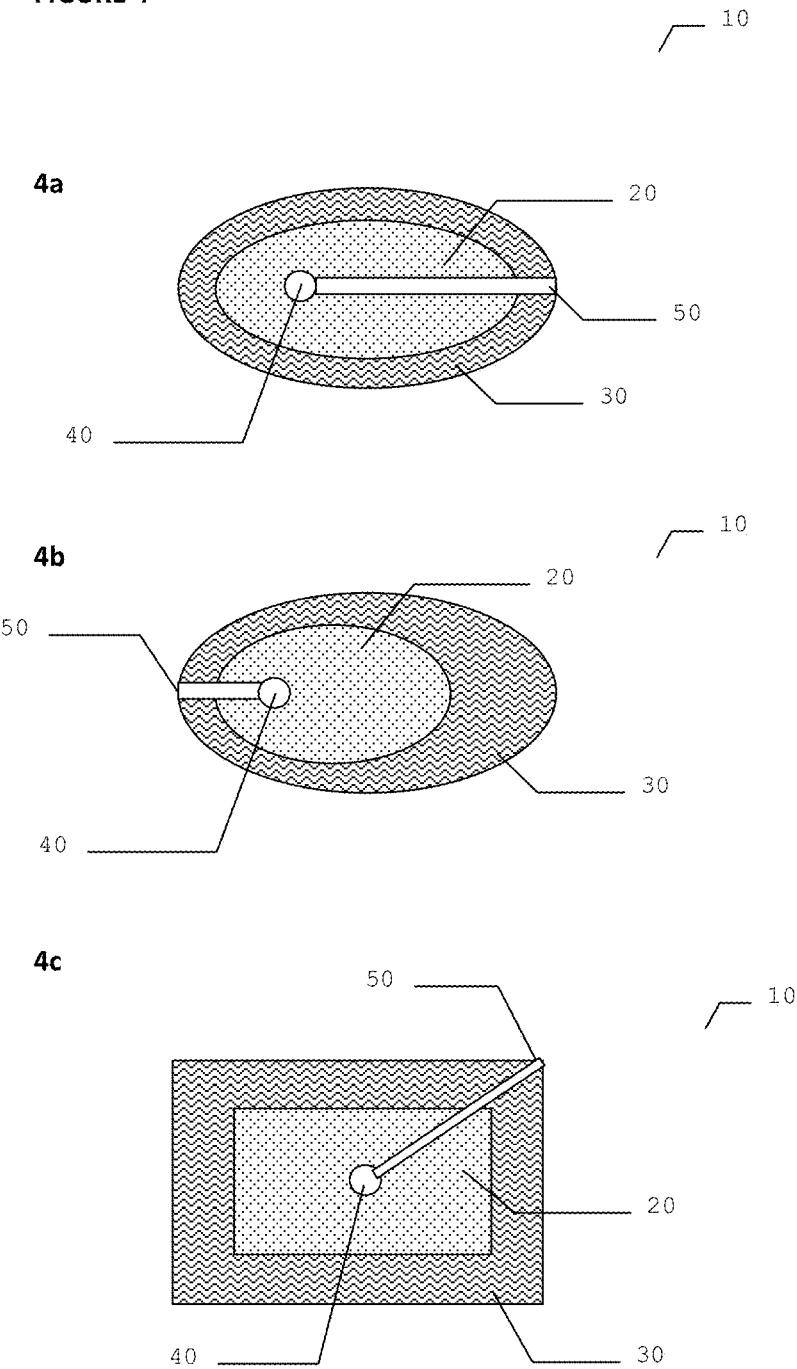
FIGS. 4a-4c illustrate perspective views of various embodiments of the inventive dressing device comprising an aperture in the center and a slit connecting a periphery of the device with the aperture.

As illustrated in FIGS. 4a-4c, which show perspective views of other embodiments of the invention, several configurations of the aperture 40 and of the slit 50 for accommodating a percutaneous or drug delivery medical device are contemplated.

Figure 5:
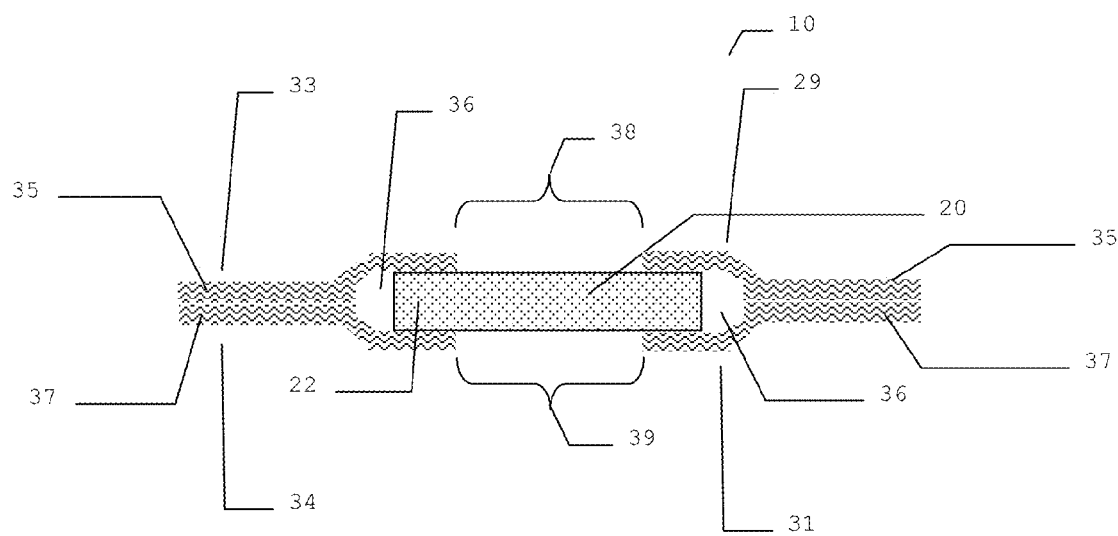
FIG. 5 illustrates a cross section view of another embodiment of a dressing device according to the present invention.

Referring to FIG. 5, a cross sectional side view of another embodiment of a dressing device 10 according to the present invention is shown. The embodiment illustrated in FIG. 5 comprises a transparent hydrogel center 20. The hydrogel center 20 can optionally comprise a bioactive agent. The embodiment in FIG. 5 further comprises an outer first absorbent material layer 35 and an outer second absorbent material layer 37. The first and second absorbent material layers 35 and 37 each comprise an absorbent woven or non-woven fabric; an internal portion 29 and 31; a peripheral portion 33 and 34; and a centrally disposed aperture 38 and 39. The first and second absorbent material layers 35 and 37 allow for expansion and contraction of the hydrogel center 20 and render a low dressing profile with a height from about 1 mm to about 5 mm. In another embodiment, the profile of the dressing device 10 is about 2 mm to about 3 mm.

The first and second absorbent material layers 35 and 37 are joined together at the peripheral portions 33 and 34 of the first and second absorbent material layers 35 and 37, and a gap 36 is formed between the first and second absorbent material layers 35 and 37 at the internal portions 29 and 31 of the first and second absorbent material layers 35 and 37. The hydrogel center 20 is disposed in the centrally disposed apertures 38 and 39 of the first and second absorbent material layers 35 and 37 and the periphery portion 22 of the hydrogel center 20 is within the gap 36 formed between the first and second absorbent material layers 35 and 37.

As can be seen in FIG. 5, the hydrogel center 20 in its peripheral part 22 is positioned and free floats between first and second absorbent material layers 35 and 37. Layers 35 and 37 are joined in the peripheral portions 33 and 34 of the first and second absorbent material layers 35 and 37 and form a gap 36 between the first and second absorbent material layers 35 and 37 at the internal portions 29 and 31 of the first and second absorbent material layers 35 and 37. The first and second absorbent material layers 35 and 37 can expand upon absorption of exudates and upon swelling of hydrogel. The hydrogel center 20 free floats between the two layers 35 and 37 of the absorbent material, which allows the hydrogel center 20 to keep its adherence to skin contour after swelling. The ratio of diameters of the hydrogel center 20 and absorbent material layers 35 and 37 and the highly fractious nature of absorbent material layers 35 and 37 allow the hydrogel center 20 to remain in the centrally disposed apertures 38 and 39 of the first and second absorbent material layers 35 and 37. In one embodiment, the ratio of diameters of the hydrogel center 20 to the absorbent material layers 35 and 37 is 1:2. In one embodiment, the outer absorbent material layers 35 and 37 are formed by two non-woven Dacron® polyester felt rings (commercially available from DuPont Inc.) needle-punched together in the peripheral portions 33 and 34 of the first and second absorbent material layers 35 and 37. The expansion gap 36 slidably engages the hydrogel center 20 in the periphery portion 22 of the hydrogel center 20.

While the prior art discloses using hydrogels attached to other layers to provide strength, and/or improve the function or securement of the hydrogel, allowing the hydrogel center 20 to free float between the two layers 35 and 37 of absorbent material improves the functional characteristics of the hydrogel center 20 and allows the hydrogel center 20 to adhere to the skin contour to provide 360 degree protection of wounds and insertion sites of percutaneous and drug delivery devices. Specifically, the design of the embodiment illustrated in FIG. 5 allows two or more dissimilar materials to optimally function at a close proximity without interfering or contaminating one another. The absorbent material of the first and second layers 35 and 37 can wick away wound exudates and swell without being constrained or deformed by the hydrogel center 20, and the hydrogel center 20 can control the release of bioactive agent(s) independent of the absorbent material. This embodiment also allows the hydrogel center 20 to be loaded with a bioactive agent(s) independent of interference from the absorbent material.

In the embodiment illustrated in FIG. 5, the inventive dressing device 10 would indicate the need for a dressing change when the first absorbent material layer 35 reveals moisture, exudates, or blood discoloration. This is a result of the design of the embodiment illustrated in FIG. 5, said design requiring the moisture and/or exudates to travel from the hydrogel center 20 to the second absorbent material layer 37, which is in contact with the surface of the wound or insertion site, prior to traveling to the first absorbent material layer 35. There is a large absorbance difference between the hydrogel center 20 and the absorbent material of the first and second layers 35 and 37 that allows the fluid to flow to the absorbent material from the hydrogel center 20. The two-layer design of the dressing device 10 in which the hydrogel center 20 separates the first and second absorbent material layers 35 and 37 allows the moisture and/or exudates to travel from layer 37 to layer 35. When the appearance of layer 35 changes, the dressing is fully or almost fully saturated from moisture and/or exudates, thus indicating a time for dressing change.

The absorbent material of the first and second absorbent material layers 35 and 37 is used to surround the hydrogel center 20. When the dressing device 10 is placed on a wound or insertion site the moisture and/or exudates is wicked in a horizontal direction until the limit of the outer diameter of the hydrogel center 20. At the outer diameter of the hydrogel center 20, the moisture and/or exudates can make intimate contact with the first absorbent material layer 35. This results in layer 35 having a moisture ring.

Referring to FIGS. 6a and 6b, illustrated are cross sectional views of another embodiment of the inventive dressing device 10 shown in FIG. 5 further comprising an optional transparent film 60 between the hydrogel center 20 and the first and second absorbent material layers 35 and 37. The transparent film 60 prevents sticking of the hydrogel center 20 to the absorbent material of the first and second layers 35 and 37, and comprises a semi-permeable polyurethane material such as film DM 4004 and DM 4007 from DermaMed Coatings Company, LLC, Hydrothane AR25-85A from CT Biomaterials, semi-permeable polyurethane from the 3M Company, or comparable materials. Other suitable materials include plastic release covers, nylon mesh and coated mesh. The transparent film 60 can be applied post casting and cross linking of the hydrogel. The thickness of the transparent film 60 film is from about 0.03 mm to 0.25 mm depending on the moisture permeability and support required for the medical or hygiene application the dressing is intended for. In another embodiment, the thickness of the transparent film 60 is between 0.05 mm and 0.15 mm.

In the embodiment shown in FIG. 6a, the transparent film 60 is disposed in the form of rings between peripheral portion 22 of the hydrogel center 20 and the peripheral portions 33 and 34 of the first and second absorbent material layers 35 and 37 leaving the central area 21 of the wound contacting side of the hydrogel center 20 open for wound contact. The film is in the form of rings that are precut or stamped to allow the hydrogel center 20 to be removed prior to application to the wound or puncture site. The transparent film 60 rings can be placed on the hydrogel center 20 prior to the hydrogel center 20 being positioned between the first and second absorbent material layers 35 and 37. The transparent film 60 adheres to the hydrogel center 20 as a result of the adherent nature of the transparent film 60 material. In the embodiment shown in FIG. 6b, the optional transparent film 60 is fully covering one side of hydrogel center 20 including the non-wound facing side of the hydrogel center 20 and the peripheral portion 22, while leaving central area 21 of the wound contacting side of the hydrogel center 20 open for wound contact. The central area 21 of the wound contacting side of the hydrogel center 20 can be unveiled by removing an optional protective film covering 75 from the central area of the hydrogel prior to the placement of the dressing device 10 on the wound or puncture site.

Figure 6:
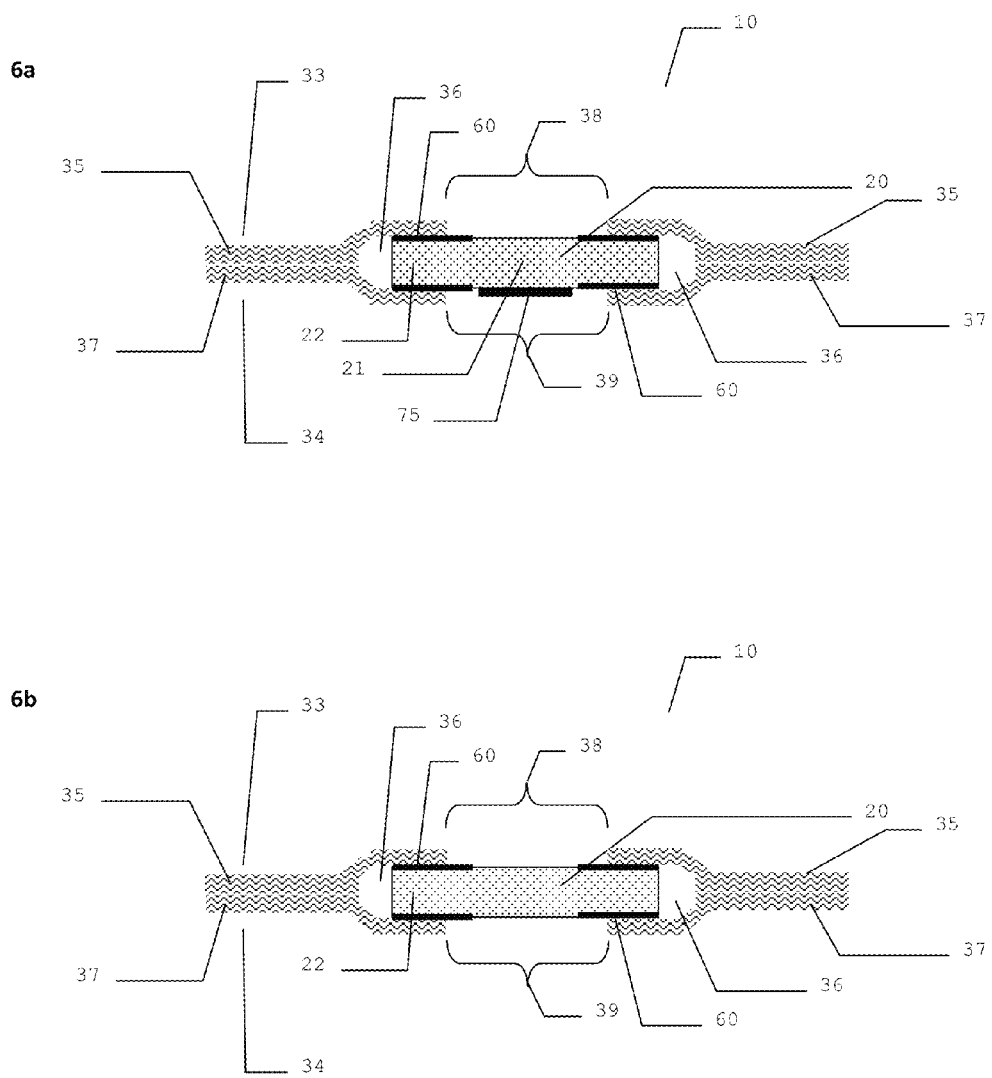
FIGS. 6a and 6b illustrate cross section views of another embodiment of the inventive dressing device shown in FIG. 5 further comprising a transparent film between the hydrogel center and the absorbent materials.

The embodiments illustrated in FIGS. 5 and 6 can also be adapted for use with a percutaneous or drug delivery medical device that has punctured the skin of a patient and has a portion of the percutaneous or drug delivery medical device protruding from the skin by further comprising an aperture and slit as discussed above. In one embodiment, the dressing device is assembled and then the optional slit 50 (not shown in FIG. 5 or 6) is cut radially through the hydrogel center 20 and the first and second absorbent material layers 35 and 37. In another embodiment, there is an overlapping flap on the first absorbent material layer 35 with optional attachment (not shown).

Figure 7:
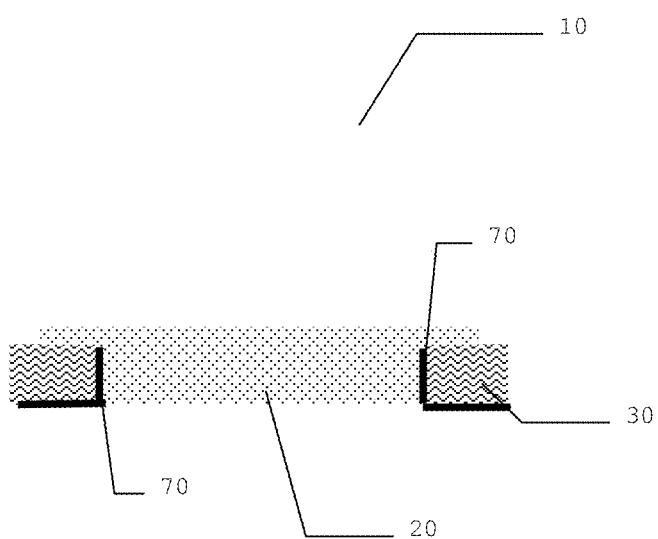
FIG. 7 illustrates a cross section view of an embodiment of the inventive dressing device further comprising a barrier coating or film.

Referring now to FIG. 7, illustrated is a cross sectional view of an embodiment of the inventive dressing device 10 with the hydrogel center 20 at least partially overlapping the absorbent material 30, with the overlap being from 10 percent to about 40 percent of the overall diameter of the device. In another embodiment, the hydrogel center 20 overlaps about 30 percent of the overall diameter of the device. The embodiment illustrated in FIG. 7 further comprises an optional barrier coating or barrier film 70 disposed at an interface between hydrogel center 20 and absorbent material 30. This optional barrier coating or barrier film 70 prevents migration of the bioactive agent into the absorbent material and comprises a polypropylene film having thickness of about 12.5 microns to about 125 microns. In this embodiment, the securement of the hydrogel to the absorbent material is achieved by partial overlap of the hydrogel over the absorbent material with the optional barrier. For example, a polyethylene oxide (PEO) hydrogel feed mix gel (AquaMed Technology Inc.) can be poured into a foam cavity, overlapping the hydrogel over the absorbent material with the optional barrier and cross linking the PEO.

The embodiment illustrated in FIG. 7 can also be adapted for use with a percutaneous or drug delivery medical device that has punctured the skin of a patient and has a portion of the percutaneous or drug delivery medical device protruding from the skin by further comprising an aperture and slit as discussed above.

Figure 8:
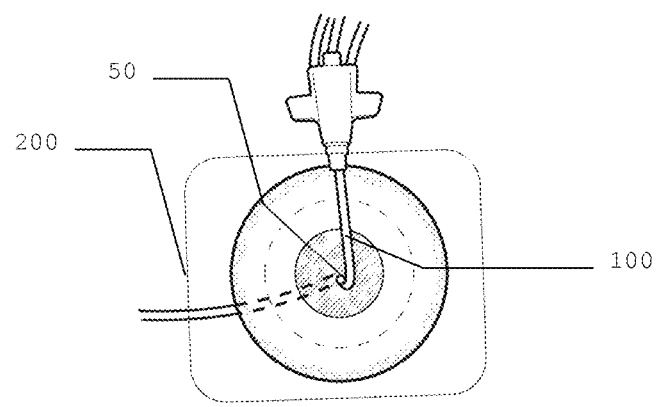
FIG. 8 is a schematic of an embodiment of the inventive dressing device dressing the insertion site of a percutaneous medical device.

Referring now to FIG. 8, a schematic view of the inventive dressing device 10 is shown with a percutaneous or drug delivery medical device 100 that has punctured the skin of a patient (not shown) and which has a portion of the percutaneous medical device 100 protruding from the skin. The optional slit 50 facilitates placement of the dressing device 10 around the percutaneous device 100. Optional dressing 200 for fixating the dressing device is fixating the dressing device 10 to the skin of patient.

One type of such a percutaneous device 100 is a catheter, such as a temporary installed catheter or longer term in-dwelling catheter.

Figure 9:
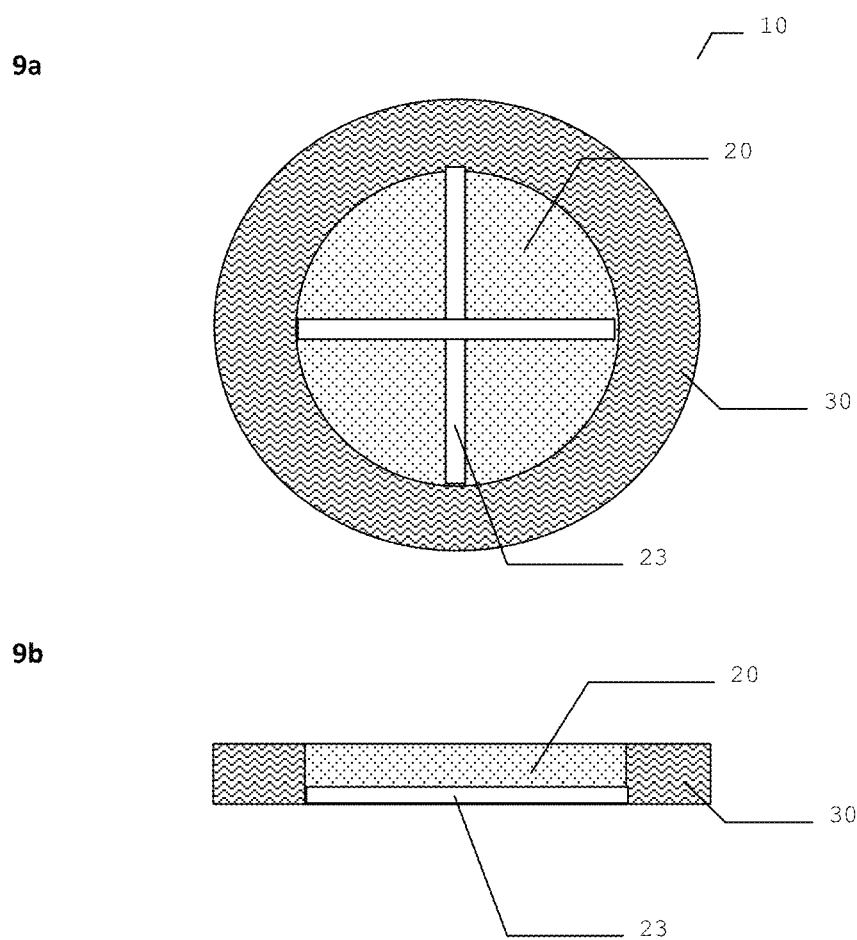

As illustrated in FIG. 9a, the hydrogel center 20 can further comprise surface channels 23 to carry exudates by capillary action towards the absorbent material. In one embodiment, the surface channels have a depth of 0.1-5 mm and a width of 0.1-5 mm. In another embodiment, the surface channels have a depth of 0.5-1 mm and a width of 0.5-2 mm. The channels are cut into the hydrogel center 20 post casting or alternatively cast into the hydrogel center 20. In FIG. 9b, a cross sectional view of the embodiment shown in FIG. 9a is illustrated. These surface channels 23 are optional for all embodiments discussed herein, FIGS. 1-7.

In another embodiment, the inventive dressing devices 10 described herein have an optional integrated transparent covering or fixation film to attach the dressing device 10 to the skin of a patient. Suitable covering or fixation films are known and available, for example the 3M Company's Tegaderm Absorbent Clean Acrylic Dressing.

In yet another embodiment, the inventive dressing devices 10 described herein further comprise a hemostatic coating, such as non-cross-linked polyethylene oxide (PEO), with the hemostatic coating disposed on the wound contacting surface of the hydrogel center 20 and/or the wound contacting surface of the absorbent material 30. In another embodiment, the hemostatic coating is dispersed in the hydrogel center 20 and/or the absorbent material 30. In the embodiment illustrated in FIGS. 5 and 6, the wound contacting surface of the hydrogel center 20 and/or the wound contacting second absorbent material layer 37 can optionally be coated with a hemostatic coating, or the hemostatic coating can be dispersed in the hydrogel center or coated on the first and/or second absorbent material layers 35 and 37. The hemostatic coating can be on a supportive fiber scrim (or mesh) which supports the hydrogel by being either incorporated into the hydrogel or bound to the surface of the hydrogel. The coating can be for example, a very thin coating of PEO having a molecular weight above about 600,000 daltons. A description of this coating, the coating of this material, and the hemostatic efficacy can be reviewed in U.S. Pat. No. 4,616,644 issued to Saferstein et al. and entitled Hemostatic Adhesive Bandage.

In another embodiment, the inventive dressing devices 10 described herein can comprise a fiber scrim or mesh to support the hydrogel center. In another embodiment, the hemostatic coating can be placed on a fiber scrim or mesh that is supporting the hydrogel center. In another embodiment, the hemostatic agent is dispersed or dissolved in the hydrogel. In an alternative embodiment, the film or mesh is made from the polyethylene oxide. In yet another embodiment, the polyurethane sponge or comparable absorbing material is coated with the high molecular weight polyethylene oxide. Other suitable materials for the optional hemostatic coating include collagen, chitosan, thrombin, gelatin, polylactic-co-glycolic acid, glycosaminoglycans/hyaluronic acid, hyaluronan, polyphenols, and comparable materials. Methods for application of a PEO coating for hemostatic applications are described, for example, in U.S. Pat. No. 4,616,644 by Saferstein et al.

Materials

The hydrogel center 20 is made of any tissue compatible hydrogel material such as polyethylene oxide (PEO), polypropylene oxide, poloxamer, 2-acrylamido-2methypropane sulphonic acid (AMPS), 3-sulphopropylacrylate (SPA), polyvinylpyrrolidone (PVP), polyethylene glycol (PEG), polylactic acid (PLA), polyvinylalcohol (PVA), polyacrylamides, silicone, agarose, methylcellulose, hyaluronan, collagen-acrylate, and polyethylene glycol (PEG) co-peptides. In one embodiment, the hydrogel material comprises PVP. In another embodiment, the hydrogel material comprises PVP with PEG and PEO.

The hydrogel material is preferably fully or partially transparent to facilitate observation of wound conditions. The hydrogel center has moisture wicking and absorptive properties with the ionic gels of the hydrogel material being able to take up moisture at an accelerated rate. This rate and capacity is less than one observes with absorbent fibers and sponges, which work by physical wicking and will release the moisture when pressure is applied. Hydrogels chemically bond the moisture and will not release the moisture with a pressure application.

The hydrogel center 20 typically does not adhere to the insertion site due to the nature of the material. The inventive dressing device requires an occlusive dressing that will help prevent microbial ingress but allow for oxygen and vapor transmission. The hydrogel can be engineered to stick intimately to the wound site by incorporating polystyrene nanoparticles into the hydrogel.

In one embodiment, the hydrogel material is prepared by the steps of cross-linking a polymer that contains chemically reactive functionalities that react with a cross-linking reagent, where the cross-linking agent comprises greater than two reactive sites per molecule that are chemically reactive with functionalities on the polymer to form a cross-linked polymer. The polymers that are to be reacted with a cross-linking agent can include PVP/PEG 0.03 inch, 10 percent PEO 0.055 inch thickness, and 5.5 percent PEO 0.055 inch thick (available from AquaMed Technologies Inc.) A PEG hydrogel material can be produced, for example, by reacting poly(ethylene glycol)-dimethacrylate (PEGDM) with a photoinitiator exposed to 365 nm ultraviolet light.

NU-GEL® Wound Dressing is an occlusive hydrogel sheet dressing consisting of preserved polyvinyl pyrrolidone in water. This formulation allows the dressing to absorb 50 percent more exudate than traditional hydrogel dressings, and is commercially available from Johnson&Johnson Wound Management a division of ETHICON, INC. Somerville N.J. First Water Limited (Marlborough, Wiltshire UK) also markets a commercially available ionic hydrogel wound dressing.

The hydrogel center 20 can be formed by molding or casting before cross-linking or by cutting after cross-linking. The cross-linked polymer can then be loaded with a desired bioactive agent(s). After being formed into the desired shape, the cross-linked polymer is contacted with a bioactive agent to reversibly bind the bioactive agent to the cross-linked polymer to form the polymeric delivery vehicle. Typically, the bioactive agent is dissolved in a suitable solvent and then placed in fluid contact with the cross-linked polymer by immersion. The loading of the polymer, which can be a synthetic or biopolymer or mixture thereof, (optionally cross-linked polymer) may be readily determined based upon the uptake of the polymer of the bioactive agent. In one embodiment, the bioactive agent is dissolved in water at a suitable concentration, typically about 1 tot percent by weight, and the cross-linked polymer is immersed therein for a period of about 20 minutes to 60 hours. In one embodiment, the cross-linked polymer is immersed for about 5-10 hours. At ambient temperature, about 20-25 degrees Celsius, the polymer is then extracted from the solvent, allowed to air dry or lyophilized, and then ready for use. The polymer is partially dry in about 2 to about 100 hours, typically 20-60 hours at ambient temperature. The time to hydrate the polymer is typically about 2 to 24 hours.

Alternatively, the cross-linked polymer may be loaded with a bioactive agent, then dried and cut to a suitable form for use. In another embodiment, the bioactive agent and polymer are dissolved in an aqueous solvent before cross-linking and the bioactive agent is bound to the polymer. Typical agent: polymer weight ratios are in the range of about 1:100 to 5:100 in solution. In another embodiment, the agent:polymer weight ratios range is 3:100. The polymer is then cross-linked by treatment with the cross-linking agent.

The antimicrobial or bioactive agent that can be incorporated in the hydrogel center 20 can be a chlorhexidine compound, for instance chlorhexidine gluconate or chlorhexidine acetate; silver compounds, for instance silver iodide, silver bromide, silver chloride, or nano-particulate metallic silver; benzalkonium chloride; polyhexamethylene biguanide (PHMB); triclosan; antibiotics such as metronidazole; alcohol; iodine; or other known antimicrobial compounds and combinations thereof that are compatible with skin and useful against a range of microorganisms, for example against known skin flora such as *Staphylococcus aureus* and methicillin-resistant *Staphylococcus aureus* (MRSA). In one embodiment, the bioactive agent is chlorhexidine gluconate, an agent known to be safe and effective and widely used as a surgical disinfectant. Plasticizers, colorants, surfactants, and stabilizers, singular or in combination, can also be incorporated in the hydrogel center.

The outer absorbent material 30 and first and second absorbent material layers 35 and 37 are made of any tissue compatible absorbent woven or non-woven material or foam. The absorbent material may comprise a felt, such as polyurethane foam; polyester mats, such as DACRON® polyester fiber mats that are commercially available from DuPont, Inc.; natural, synthetic, or hybrid synthetic/natural polyester; cellulose; alginate; polyacrylates; polyolefins; and cottons.

The thickness of the polymeric matrix may be varied as desired, depending upon the desired pharmaceutical dosage and duration of delivery. Ordinarily, a suitable matrix thickness will be in a range of about 0.25 to 5 mm. In one embodiment, the suitable matrix thickness is 0.5 mm to 1.5 mm.

In one embodiment, the diameter of the dressing device ranged from 2 cm to 10 cm with a ratio of diameters of the hydrogel center to absorbent material at approximately 1:2. In another embodiment, such as that illustrated in FIG. 5, the dressing device is 1 mm thick with an outside diameter of 50 mm and an inside diameter of 25 mm, and the hydrogel center 20 is 0.4 mm thick with an outside diameter of 35 mm. In another embodiment, the wound facing side of the hydrogel center has a 20 to 25 mm area where a polyethylene protective film would be removed prior to wound application.

Percutaneous Medical Devices

Percutaneous medical devices for which the dressing devices of the present invention can be used include catheters, pins, implants, and the like which pass through the skin and are indwelling for some considerable time. Exemplary of percutaneous medical devices are central venous catheters, peripheral venous catheters, Swan-Ganz pulmonary catheters, central nervous system implants, such as external ventricular drainage and ventricular reservoirs, peritoneal dialysis catheters, such as for continuous ambulatory peritoneal dialysis and continuous cyclic peritoneal dialysis, hemodialysis catheters, transvenous pacemaker leads, and temporary orthopedic pins. All of these percutaneous medical devices, when in place, have a portion of the device that is external and left protruding from the skin, which can be the cause of infection around the insertion sites of the medical devices.

Method

The present invention also relates to a method of dressing the wound site or the insertion site of a percutaneous or drug delivery medical device for a patient using such a device. The inventive dressing device can optionally have a bioactive agent that is incorporated into the device and/or onto the lower or wound/skin facing surfaces of the device, wherein the device is secured to the surface of skin and optionally to the percutaneous medical device with the help of an adhesive overdressing layer preferably in the form of adhesive thin film or adhesive bandaging tape.

When used over a wound, the dressing device 10 is applied by positioning the device over the wound with the hydrogel center 20 facing the wound and in contact with the wound, and the outer absorbent material 30 (or first and second absorbent material layers of the embodiment illustrated in FIGS. 5 and 6) on the periphery of the wound or surrounding the wound, with any blood and exudates absorbed by the absorbent outer material 30.

When used over a percutaneous or drug delivery medical device, the dressing device 10 is applied by positioning the dressing device with the hydrogel center 20 facing the skin and with the percutaneous or drug delivery device guided through the slit 50 and into the aperture 40, enabling the dressing device to fully surround the catheter at the insertion or puncture site. The hydrogel center 20 is thereby in contact with the skin surrounding the puncture site. Advantageously, the dressing device enables nurses and physicians to position the dressing device over a previously installed or secured percutaneous or drug delivery medical device, such as a catheter. The dressing device provides 360 degree or complete circumferential coverage around the catheter shaft and for a length greater than the diameter of the catheter shaft. In one embodiment, the dressing device is elastically resilient and it can be attached to the catheter without using an adhesive or additional dressing. In another embodiment, the dressing device has antimicrobial properties wherein the hydrogel center 20 comprises a bioactive agent(s).

The following examples are illustrative of the principles and practice of this invention, although not limited thereto. Numerous additional embodiments within the scope and spirit of the invention will become apparent to those skilled in the art once having the benefit of this disclosure.

EXAMPLE 1

Materials

Antimicrobial dressing devices as illustrated in FIG. 5 were assembled using several types of hydrogel materials: hydrogel from Aquamed Technologies PVP/PEG 0.03 inch, 10 percent PEO 0.055 inch thickness, 5.5 percent PEO 0.055 inch thick; hydrogel from NU-GEL® Wound Dressing which is an occlusive hydrogel sheet dressing consisting of preserved polyvinyl pyrrolidone in water; and ionic hydrogel from First Water Wiltshire in UK. The three types of hydrogels were used to assemble the inventive devices, but only the devices with Nu-Gel hydrogel were used to test the antimicrobial properties.

Two DACRON® nonwoven polyester mats were used for the first and second absorbent material layers.

Preparation of First and Second Absorbent Material Layers with a Gap

To make approximately 50 prototype devices, appropriate quantities of Dacron® nonwoven polyester mats, obtained from DuPont Inc., were cut to size having a thickness of 1 mm thick (but thicknesses of from about 0.5 mm to about 2.5 mm can be utilized), a diameter of 50 mm, and a 20 mm centrally disposed aperture. For each prototype device, two Dacron® nonwoven polyester mats were melded together by needle punching in their peripheral portions to bring the mats into intimate contact to allow moisture to transverse the layers and to remain integral during application and throughout treatment duration. A gap or sock like structure was formed between the two layers at their internal portions. The barb needle was able to combine the two layers together by interspersing the non woven fibers between the two layers.

Preparation of the Hydrogel Material with a Bioactive Agent

One way of loading the hydrogel material with a bioactive agent(s) is adding the bioactive agent(s) into the feed mix (which is the non-cross-linked hydrogel material) and mixing until fully homogeneous prior to cross-linking. The cross-linking is then performed by any methods known to these skilled in the art, e.g. UV, e-beam, thermal, etc. In the instant invention, the commercial hydrogel was used and prepared by cutting to a specific size.

The hydrogel material for the hydrogel center was cut to form a 3.5 cm diameter disk and then loaded with 40 mg CHG. Specifically, CHG in a 20% CHG solution in water was loaded on a Nu-GEL® Wound Dressing which is a polyvinyl pyrrolidone hydrogel supported by a supportive fiber scrim (or mesh) with a polyethylene film on both outer surfaces. The hydrogel was removed from the sterile foil package and had the bottom protective polyethylene film removed to allow partial dehydration to take place. The hydrogel was stored at ambient conditions and allowed to lose about 8 to 10% of its equilibrium weight. 2 ml of the CHG solution was distributed on the hydrogel surface and allowed to be drawn in. The hydrogel was then observed to recover to its original hydrated weight.

Octendine 20% in EtOH solution was loaded on another Nu-GEL® Wound Dressing. The hydrogel was removed from the sterile foil package and had the bottom protective polyethylene film removed to allow partial dehydration to take place. The hydrogel was stored at ambient conditions and allowed to lose about 8 to 10% of its equilibrium weight. 2 ml of the Octendine 20% EtOH solution was distributed on the hydrogel surface and allowed to be drawn in. The hydrogel was then observed to recover to its original hydrated weight.

PHMB 20% solution in water was loaded on another Nu-GEL® Wound Dressing. The hydrogel was removed from the sterile foil package and had the bottom protective polyethylene film removed to allow partial dehydration to take place. The hydrogel was placed at ambient conditions and allowed to lose about 8 to 10% of its equilibrium weight. The PHMB 20% solution in water was distributed on the hydrogel surface and allowed to be drawn in. The hydrogel was then observed to recover to its original hydrated weight.

20% CHG in water+Octendine 20% solution in ethanol was loaded on another Nu-GEL® Wound Dressing. The hydrogel was removed from the sterile foil package and had the bottom protective polyethylene film removed to allow partial dehydration to take place. The hydrogel was placed at ambient conditions and allowed to lose about 8 to 10% of its equilibrium weight. The 20% CHG+Octendine 20% solution was then distributed on the hydrogel surface and allowed to be drawn in. The hydrogel was then observed to recover its original hydrated weight.

Assembly of the Device

At least 50 hydrogel centers prepared as discussed above were disposed in the centrally disposed apertures of the first and second absorbent material layers made of Dacron® nonwoven polyester mats (prepared as discussed above). The periphery portion of the hydrogel center free floats within the gap formed between the first and second absorbent material layers. To ensure the hydrogel remained hydrated, the assembled device was placed in a foil pouch. Sterilization would be by radiation.

ZOI Study

Two prototypes were then evaluated in a Zone of Inhibition (ZOI) study. The ZOI assay was performed on a Tryptic soy agar (TSA) plate with 6 Log/plate by surface inoculation. ZOI was defined as distance in millimeters between the edge of the device and edge of the no growth zone. Sustained efficacy against *S. aureus* was tested by daily transfer to a new inoculated plate. The tested devices, both loaded with CHG as the bioactive agent, demonstrated sustained in vitro efficacy of 7 days against *S. aureus* as shown in Table 1. Two samples utilizing Nu-Gel hydrogel were tested, and the results in Table 1 are an average of the two samples.

TABLE 1

Zone of Inhibition against *S. aureus*

| Time | ZOI (mm) *S. aureus* |
|---|---|
| Day-1 | 6.6 |
| Day-2 | 6.3 |
| Day-3 | 5.9 |
| Day-4 | 5.1 |
| Day-5 | 4.8 |
| Day-6 | 4.5 |
| Day-7 | 3.8 |

EXAMPLE 2

Ten prototype devices made as described in Example 1 were evaluated for blood or serum absorbency when positioned on fresh pig skin. The samples were not loaded with bioactive agent, and the hydrogel used was Nu-Gel. Pig skin was dried with paper towels, cut into 8×8 cm squares, and placed into Petri dishes. Various and clinically relevant volumes of blood or serum were added on the center of the pig skin squares, then BIOPATCH® or a prototype device was applied on top of the fluid. The fluid absorption time and device appearance were observed and recorded.

The results of one typical test on one device are shown in Table 2. The prototypes showed equivalent or better absorbency compared to the BIOPATCH® cuff commercially marketed by Johnson & Johnson Corporation. The hydrogel center remained transparent after the prototype devices absorbed whole blood or serum to the point of saturation. The rate of absorption of the prototype is comparable to that of BIOPATCH®. The observed rate of absorption for both BIOPATCH® and the prototype device was about 2 g of blood or serum per minute.

TABLE 2

|  | BIOPATCH ® | Prototype Device |
|---|---|---|
| Weight (g) | 0.3447 g | 1.3522 g |
| Applied on top of 2 ml blood | complete absorption in 1 min | completely absorbed in 1 min, center visible |
| Applied on top of 3 ml blood | complete absorption in 1.5 min | completely absorbed in 1.5 min, center visible |
| Applied on top of 4 ml serum | abort 0.5 ml left after 2 min and saturation | completely absorbed in 1.5 min, center visible |

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

We claim:

1. A wound dressing comprising:
   a transparent hydrogel center comprising a periphery portion;
   a first absorbent material layer comprising:
      an internal portion;
      a peripheral portion; and
      a centrally disposed aperture; and
   a second absorbent material layer comprising:
      an internal portion;
      a peripheral portion; and
      a centrally disposed aperture;
   wherein the first and second absorbent material layers are joined together at the peripheral portions of the first and second absorbent material layers and a gap is formed between the first and second absorbent material layers at the internal portions of the first and second absorbent material layers;
   wherein the hydrogel center is disposed in the centrally disposed apertures of the first and second absorbent material layers and the periphery portion of the hydrogel center is within the gap formed between the first and second absorbent material layers.

2. The wound dressing of claim 1, further comprising an aperture in the hydrogel center and a slit connecting the peripheral portions of the first and second absorbent material layers with the aperture in the hydrogel center.

3. The wound dressing of claim 2, wherein a diameter of the aperture in the hydrogel center is from about 0.3 mm to about 15 mm.

4. The wound dressing of claim 2, wherein a width of the slit is from about 0.01 mm to about 2 mm.

5. The wound dressing of claim 2, wherein the slit is non-linear.

6. The wound dressing of claim 1, wherein the first and second absorbent material layers comprise a woven or non-woven felt or foam selected from the group consisting of polyurethane, polyester, cellulose, alginate, polyacrylates, polyolefins, and cottons.

7. The wound dressing of claim 1, wherein the hydrogel center comprises a hydrogel material selected from the group consisting of polyethylene oxide, polypropylene oxide, poloxamer, 2-acrylamido-2methypropane sulphonic acid, 3-sulphopropylacrylate, polyvinylpyrrolidone, polyethylene glycol, polylactic acid, polyvinylalcohol, polyacrylamides, silicone, agarose, methylcellulose, hyaluronan, collagen-acrylate, and polyethylene glycol co-peptides.

8. The wound dressing of claim 1, wherein the hydrogel center free floats in the gap between the first and second absorbent material layers.

9. The wound dressing of claim 1, wherein the hydrogel center comprises a bioactive agent.

10. The wound dressing of claim 9, wherein the bioactive agent comprises one or more antimicrobial agents selected from the group consisting of chlorhexidine gluconate, chlorhexidine acetate, silver iodide, silver bromide, silver chloride, nano-particulate metallic silver, benzalkonium chloride, polyhexamethylene biguanide, Triclosan, metronidazole, alcohol, or iodine.

11. The wound dressing of claim 9, wherein the bioactive agent is chlorhexidine gluconate.

12. The wound dressing of claim 1, wherein the hydrogel center further comprises a plurality of surface channels.

13. The wound dressing of claim 1, wherein the hydrogel center further comprises a hemostatic coating.

14. The wound dressing of claim 13, wherein the hemostatic coating is disposed on a wound contacting surface of the hydrogel center.

15. The wound dressing of claim 13, wherein the hemostatic coating is non-cross-linked polyethylene oxide.

16. The wound dressing of claim 1 further comprising a transparent film disposed between the hydrogel center and the first and second absorbent material layers.

17. The wound dressing of claim 16, wherein the transparent film is in the form of rings.

* * * * *